United States Patent
Mendes et al.

(10) Patent No.: US 6,391,341 B1
(45) Date of Patent: May 21, 2002

(54) GASTRORESISTANT MULTI-UNITARY PHARMACEUTICAL PREPARATIONS CONTAINING PIROXICAM

(76) Inventors: Carla Patricia Goncalves Mendes, Av. Estado da India, Quinta do Patrimonio Lote 12-12 "B"; Maria Julia Caeiro Ramalho de Oliveira, Real do Forte, Lote 10-2 D, both of 2685 Sacavem (PT)

( * ) Notice: Subject to any disclaimer, the term of this patent is extended or adjusted under 35 U.S.C. 154(b) by 0 days.

(21) Appl. No.: 09/580,552

(22) Filed: May 30, 2000

(30) Foreign Application Priority Data

Dec. 16, 1999 (EP) ............................................. 99670011

(51) Int. Cl.$^7$ ............................. A61K 9/14; A61K 9/16; A61K 9/50

(52) U.S. Cl. ........................ 424/489; 424/400; 424/439; 424/451; 424/464; 424/468; 424/472; 424/490; 514/951; 514/964; 514/965

(58) Field of Search ................................ 424/400, 439, 424/464, 474, 489, 490, 497; 514/825, 886, 951, 960, 964, 965

(56) References Cited

U.S. PATENT DOCUMENTS 5,814,338 A * 9/1998 Veronesi ...................... 424/472
5,958,458 A * 9/1999 Norling et al. .............. 424/490

* cited by examiner

Primary Examiner—Thurman K. Page
Assistant Examiner—Charesse L. Evans
(74) Attorney, Agent, or Firm—Sughrue Mion, PLLC

(57) ABSTRACT

The present invention relates to multi-unitary pharmaceutical preparations containing piroxicam for oral administration. Such pharmaceutical preparations are stable pellet pharmaceutical preparations containing piroxicam and they comprise an amount of active ingredient of between 5 and 50 mg, an inert core with spherical symmetry and a diameter of 600–850 μm, constituted by inert excipients, coated with an active layer containing piroxicam in micronized form and various pharmaceutically acceptable inert excipients, mixed in appropriate proportions in order to allow the adequate disaggregation of the formulations and dissolution of the active ingredient, coated in it turn with an insulating layer of a polymeric nature and soluble in water, this layer being coated finally with a gastroresistant or enteric layer of a minimum thickness of 20 μm. This invention also refers to the process for the preparation of said pharmaceutical preparations.

9 Claims, 2 Drawing Sheets

Graphic representation of the results obtained for the stability tests carried out at 40°C/75% relative humidity with a batch of piroxicam pellets.

Graphic representation of the results obtained for the stability tests carried out at 40°C/75% relative humidity with a batch of piroxicam pellets.

Graphic representation of the results obtained for the stability tests carried out in real time with a batch of piroxicam pellets.

GASTRORESISTANT MULTI-UNITARY PHARMACEUTICAL PREPARATIONS CONTAINING PIROXICAM

FIELD OF THE INVENTION

The present invention relates to multi-unitary pharmaceutical preparations containing piroxicam for oral administration. The formulations comprise a spherical inert core, constituted by starch and sugars, coated with a layer containing the active ingredient in micronized form, which is mixed with pharmaceutically acceptable inert excipients, whose proportions are suitable for allowing the disaggregation of the dosage forms and the intended dissolution of the active ingredient, this layer in turn being coated with an insulating polymeric layer, applying lastly a gastroresistant or enteric external layer, of suitable thickness, in order to guarantee the integrity of the product until it reaches the proximal part of the small intestine, where the formulation will be disaggregated to facilitate the absorption of the piroxicam. The pellets produced according to the invention are placed in hard gelatine capsules and administered under this form. The invention allows the oral administration of piroxicam, preventing the adverse gastrointestinal disturbances and ulcerogenic effects of piroxicam generally associated with chronic use, because the piroxicam is only delivered at the proximal portion of small intestine and this is an advantage in relation to the other pharmaceutical preparations of piroxicam for oral administration. Besides, the pharmaceutical product prepared according to the invention is free from organic solvents and/or the impurities generally associated to them, because the application of the different layers exclusively requires aqueous solvents. This aspect constitutes a technological advantage, since the manufacturing process is safe, because there is no toxicity risk to operators or explosion risks, and it is much more ecological, because there is no possibility of environmental contamination caused by organic solvents leaking into the atmosphere. Finally, it is much safer for the patient, because there is no need to consider solvent and/or residual impurities associated to them, which is a considerable advantage in terms of public health. For the manufacture of the product, only one equipment is required—a fluid bed equipment with an inner partition device (wurster). The products obtained by extrusion/spheronization, by rotogranulation or by "powder coating" are completely outside the scope of this invention. The products obtained are stable for a period of time compatible with pharmaceutical requirements and present gastroresistance and dissolution characteristics generally adapted to the period of validity established for pharmaceutical products (i.e. 3 years).

BACKGROUND OF THE INVENTION

Piroxicam, whose chemical name is N-(2-pyridyl)-2-methyl-4-hydroxy-2H-1,2-benzothiazine-3-carboxyamido-1,1-dioxide, is a nonsteroidal anti-inflammatory drug (NSAID) described and claimed by J. G. Lombardino in the patent U.S. Pat. No. 3,591,584. It possesses excellent anti-inflammatory and analgesic properties and is widely used in the treatment of arthritic and rheumatic diseases, namely osteoarthritis and rheumatoid arthritis. For these indications, it is normally administered orally. However, piroxicam has various side effects, including gastrointestinal disorders and ulcerogenic effects generally associated with its chronic use. In chronic use, with high dosages and especially in the elderly, NSAIDs can induce stomach ulcers that may be dangerous. Such ulcers generally show little or few symptoms and may cause serious bleeding when undetected. Accordingly, when inflammatory symptoms become less severe, it is often desirable to apply piroxicam topically. Nevertheless, in acute cases, oral or rectal administration is most suitable. However, rectal administration is not functional, is very uncomfortable and is not favoured by patients. It is also well known that oral administration is the best way of making patients follow the therapeutic treatment. For this reason, various efforts have been made to minimize the adverse effects of NSAIDs when administered orally. Several authors have tried to solve the problem of the gastric lesions produced by oral NSAID pharmaceutical preparations:

EP-0 288 138 describes multi-particulate pharmaceutical compositions containing water-insoluble drugs dispersed in a controlled release matrix. Preferred drugs are NSAIDs, especially calcium fenprofen, ibuprofen, ketoprofen, naxoprofen, sodium diclofenac, fenbufen, flurbiprofen, indomethacin, oxyphenbutazone, phenylbutazone and piroxicam. These pharmaceutical compositions are multi-unitary and drug release occurs in the gastric region, contrary to what is intended with the present invention.

EP-0123520 describes processes for preparing piroxicam salts and pharmaceutical dosage forms from which the piroxicam is rapidly absorbed in the gastrointestinal tract after administration.

U.S. Pat. No. 5,654,002 describes a process for the production of conventional piroxicam tablets.

U.S. Pat. No. 5,015,481 describes a pharmaceutical tablet composition, which is an admixture of an NSAID, diclofenac or piroxicam, a prostaglandin and hydroxypropylmethylcellulose in order to maintain the prostaglandin in a therapeutically active amount to allow the prevention of NSAID-induced ulcers.

U.S. Pat. Nos. 5,601,843 and 5,698,225 describe pharmaceutical tablet compositions including a core of an NSAID selected between diclofenac and piroxicam which is surrounded by a mantle coating of a prostaglandin, wherein an intermediate coating can also be present between the NSAID core and the prostaglandin mantle.

Prostaglandins are generally considered to be highly unstable and difficult to provide in orally-available stabilized forms. The association of prostaglandins with NSAIDs is a factor of increased stability for both drugs. On the other hand, this association implies the administration of two active ingredients instead of just one, which represents an inadvisable overload for the metabolism of the patient.

The present invention describes multi-particulate gastroresistant coating dosage forms to prevent the delivery of the piroxicam in the gastric compartment and allow its release at the proximal portion of small intestine, preventing gastric lesions resulting from the direct contact of piroxicam with gastric mucous. The multi-unitary dosage form, after dissolution of the enteric coating, rapidly disperses and releases the piroxicam, which is immediately absorbed through the membranes of the small intestine. The present invention concerns stable multi-unitary pharmaceutical compositions for oral administration consisting of gastroresistant pellets free from residues of organic solvents and the impurities associated to them. This piroxicam formulation is new, taking into account the current state of the art. Its manufacturing process involves the use of only one equipment for all the stages of its production, which is a fluid bed equipment with an inner partition device (wurster). Thus, the present invention describes pellet formulations composed of an inert core coated with a layer containing the active ingredient piroxicam, coated in turn with an intermediate layer which is coated finally with an external gastroresistant or enteric coating layer of a minimum thickness of 20 µm. The presence of the intermediate layer is important for the rapid dissolution of the final product. The pellets obtained have spherical symmetry and their surface is perfectly flat, when observed by scanning electronic microscopy (S.E.M.), contrary to what happens when other techniques are used, like powder coating, extrusion/spheronization or coating in conventional coating pans. In addition, the fact that the products are manufactured without the aid of organic solvents makes them safer for patients and for operators who manufacture and handle them. The manufacturing process does not cause environmental pollution problems, which are becoming increasingly essential to avoid. Moreover, the process for manufacturing these new formulations has technical as well as economic advantages. In fact, all the stages of the manufacturing process use the same equipment, which represents less contact for the operator with the product, contrary to what generally happens with other processes which require the transfer of the pellets from the extruder/spheronizer to coating pans or fluid bed equipments in order to be coated. Neither does it involve various equipments of restricted use and a high price, which would have to be reflected in the final price of the product to consumers and be borne by patients who need the medication.

A particular benefit of the invention is that it provides a safe method for treating inflammation with piroxicam without gastric sequelae, it permits chronic use and/or high dosages and, in particular, use by the elderly. Obviously, the present invention could be applied to other high potency NSAIDs.

SUMMARY OF THE INVENTION

The present invention describes multi-unitary pharmaceutical dosage forms containing piroxicam constituted by a succession of layers arranged around an inert, spherical core, prepared in a fluid bed equipment with an inner partition device (wurster). The component elements of the dosage form are:
(1) Inert core,
(2) Active layer,
(3) Insulating layer and
(4) Gastroresistant or enteric coating layer.

The inert cores of dimensions of 600–710 µm or 710–850 µm, constituted by inert excipients, are coated with a layer containing piroxicam mixed with pharmaceutically acceptable inert excipients, making this layer quickly disaggregable. This layer is then coated with an insulating layer of a polymeric nature, which is coated finally with an gastroresistant coating layer of a minimum thickness of 20 µm. The pellets have spherical symmetry and a flat surface, are free from residues of organic solvents and the impurities associated to them and they have a moisture level that guarantees good stability under normal storage conditions. The pellets are placed in hard gelatine capsules and it is in this form that they are administered to patients. The formulations with this composition are characterized in that they do not dissolve in an acid medium, but dissolve quickly at an alkaline pH and present good stability in terms of dosage and in gastroresistance and dissolution assays, when stored for at least 3 years.

BRIEF DESCRIPTION OF THE DRAWINGS

In order to test the stability of the finished product in its packaged form, an industrial batch of piroxicam pellets was prepared (i.e. 400,000 capsules), which were placed inside hard gelatine capsules, which were in turn stored in polyamide/aluminium/PVC blisters sealed with aluminium foil of 25 µm. The blisters were incubated in climatic chambers at 25° C. and 60% relative humidity (atmospheric conditions) and 40° C. and 75% relative humidity (accelerated assays). The following parameters were periodically determined: dosage, gastroresistance, dissolution and level of impurities.

DETAILED DESCRIPTION OF THE INVENTION

Figure 1:
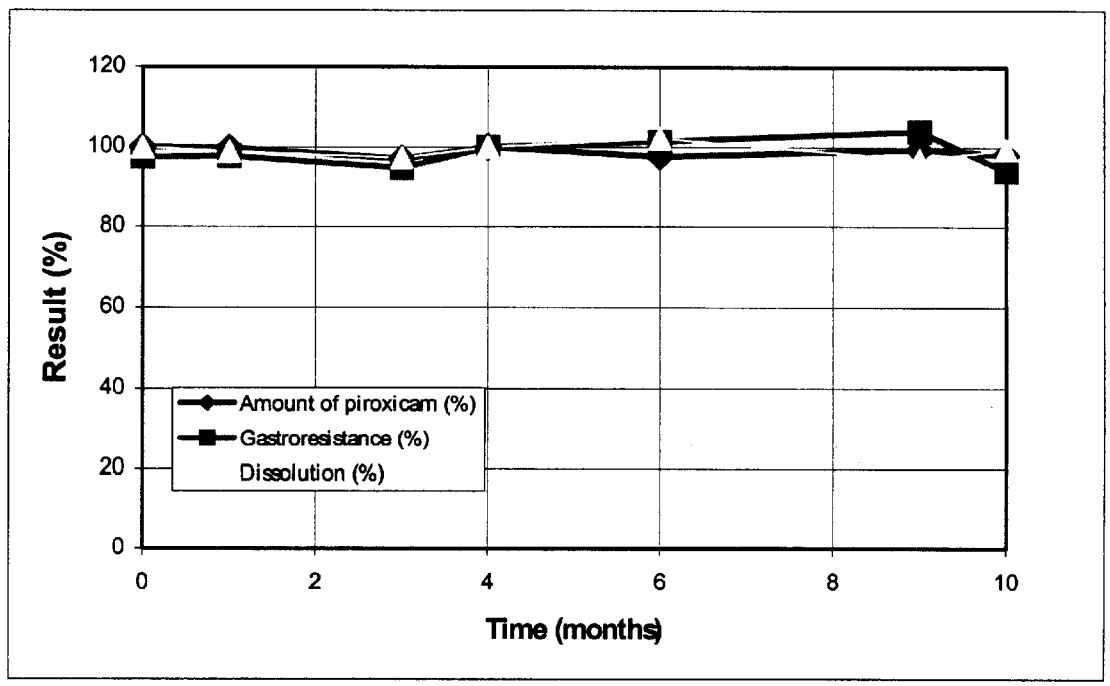
FIG. 1 shows a graph of the dosage, gastroresistance and dissolution results obtained when the blisters are stored at 40° C. and 75% relative humidity (accelerated assays) for 10 months. As can be seen, the piroxicam content is never lower than 95%, which is the minimum amount generally admissible for the amount of active ingredient in pharmaceutical forms during the period of validity. As can also be seen in FIG. 1, the gastroresistance value obtained for the period during which the assay was carried out was never lower than 85%, which is the minimum percentage generally accepted for gastroresistant formulations during the period of validity. Also as regards the dissolution assay, the value determined for this parameter for the period during which the assay was carried out was never lower than 75%, which is the minimum value generally accepted for this type of formulation during the period of validity. The values obtained for each of the parameters studied are presented in detail in Table V.
Figure 2:
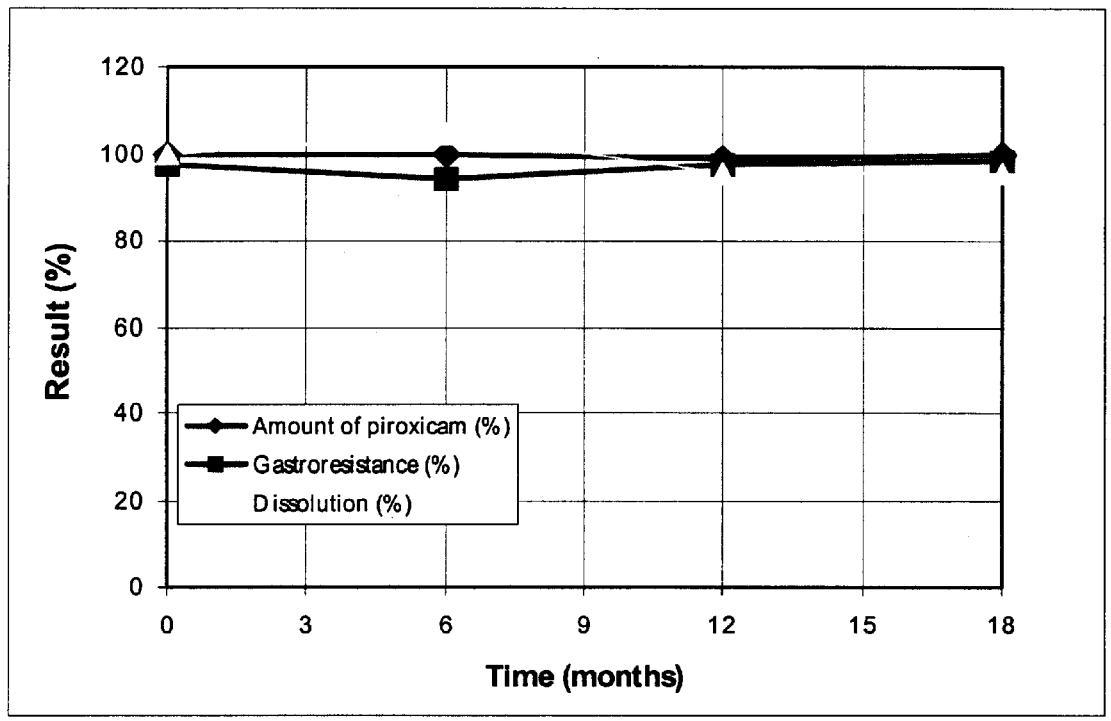
FIG. 2 shows a graph of the dosage, gastroresistance and dissolution results obtained when the blisters are stored at 25° C. and 60% relative humidity (assays in real time or under atmospheric conditions) for 18 months. As can be seen, the piroxicam content is never lower than 95%, which is the minimum amount generally admissible for the dosage of active ingredient in pharmaceutical forms during the period of validity. As can also be seen in FIG. 2, the gastroresistance value obtained for the period during which the assay was carried out was never lower than 85%, which is the minimum percentage generally accepted for gastroresistant formulations during the period of validity. Also as regards the dissolution assay, the value determined for this parameter for the period during which the assay was carried out was never lower than 75%, which is the minimum value generally accepted for this type of formulation during the period of validity. The values obtained for each of the parameters studied are presented in detail in Table VI.

The present invention describes formulations that comprise an inert core of spherical symmetry constituted by pharmaceutically acceptable inert excipients, coated with a succession of layers, in order to produce final multi-unitary gastroresistant formulation (pellets) that are placed in hard gelatine capsules. Another advantage of these new formulations is that all the stages of their production take place in the same equipment and do not require the use of organic solvents. For this reason, these pharmaceutical preparations are safer for operators during their manufacture and for the patients to whom they are administered.

The elements to consider in the formulations are the following:
I. Inert cores.
II. Active layer.
III. Insulating layer.
IV. Gastroresistant or enteric coating layer.

I. Inert Cores

The inert cores have dimensions of 600–710 µm or 710–850 µm, according to the piroxicam potency that is intended in the final product. The inert cores are constituted by starch (10–30%) and sucrose (60–90%), but can also contain glucose, lactose, mannitol or any other pharmaceutically acceptable inert excipients. With solid consistency and spherical symmetry, the inert cores are obtained from sucrose particles by coating them with successive layers of sucrose and cornstarch. The final product must contain less than 4% humidity. The particles must be selected in a relatively narrow range of granulometry, so that the pellets obtained at the end are of a uniform dimension. For the piroxicam dosages generally used in therapeutics (i.e. generally 20–40 mg/capsule), the inert cores should not exceed 850 μm, so that gelatine capsules of a relatively small dimension can be used, which helps the patient adhere to the therapy being followed. The inert cores can be obtained commercially and do not constitute the aim of the present invention.

II. Active Layer

The active layer is applied to the inert core and it contains piroxicam in micronized form and pharmaceutically acceptable excipients, for example surfactant agents, such as fatty acids of sorbitane esters, like glycerol polyethyleneglycol oxystearate (Cremophor® of BASF Corporation), sodium trilaurylphosphate, sodium tridecylethoxylate, sodium myristylsulfate or, preferentially, sodium dodecyl sulfate, which increase the wetability of the micronized piroxicam; binding agents of a polymeric nature, such as hydroxymethylpropylcellulose (Pharmacoat® of Shinetsu; Methocel® of Colorcon), hydroxypropylcellulose (Klucel® of Hercules), hydroxymethylcellulose, hydroxyethylcellulose (Natrosol® of Hercules, or Cellosize® of Union Carbide Corporation), methylcellulose (Methocel® A of Colorcon), ethylcellulose (Aquacoat® of FMC or Surealease® of Colorcon), polyvinylpyrrolidone (Povidone® of GAF Corp.; Kollidon® of BASF), polyethylene glycols, etc. In order for the dosage form to dissolve quickly disintegrating agents are added, such as sodium starch glycolate (Explotab® of Mendell, Primogel® of Generichem), pregelatinized starch (Starch 1500), microcrystalline cellulose (Avicel® of FMC), sodic or calcic carboxymethylcellulose or sodium alginate. Lubricant agents as magnesium or calcium stearate or, preferentially, talc, should be added, in order to decrease the friction between the particles. The suspension containing the mixture of the ingredients is prepared exclusively in water. For the suitable preparation and application of the suspension, the inclusion of anti-foaming agents, such as simethicone, is advisable, preferentially in a form which is easily dispersible in water (in the form of an emulsion containing not less than 85% polydimethylsiloxane).

When used in the appropriate proportions, the substances previously mentioned are mixed with the active ingredient, in an aqueous solution, are atomized on the inert cores under suitable conditions, producing a uniform layer of a thickness of between 150 and 250 μm.

III. Insulating Layer

An insulating layer is applied to the active layer in order to separate the layer containing the piroxicam from the enteric coating layer. In fact, gastroresistant polymers generally have free carboxyl groups with acidic characteristics that can interact with the active ingredients of the first layer and induce unexpected changes. For this reason, an insulating layer should be inserted between the active layer and the enteric coating layer. If the active ingredient is sensitive to acidic pH, this intermediate layer needs to have a thickness of more than 15 μm, in order to prevent any contact between the active and the enteric coating layers, because the acrylic polymers contained therein have acidic groups that could degrade acid-sensitive active ingredients.

The insulating layer contains binding agents which, by virtue of the evaporation of the solvent (i.e. demineralized water), form a protective layer. The binding agents of the insulating layer should be chosen among hydroxymethylpropylcellulose (Pharmacoat® of Shinetsu; Methocel® of Colorcon), hydroxypropylcellulose (Klucel® of Hercules), hydroxymethylcellulose, hydroxyethylcellulose (Natrosol® of Hercules or Cellosize® of Union Carbide Corporation), methylcellulose (Methocel® A of Colorcon), ethylcellulose (Aquacoat® of FMC or Surealease® of Colorcon), polyvinylpyrrolidone (Povidone® of GAF Corp.; Kollidon® of BASF), polyethylene glycols, etc. The dispersion obtained, of suitable viscosity, is applied to the granules already containing the active ingredient. Other inert excipients could be added to this dispersion in order to improve or change the properties of the pellets.

IV. Gastroresistant (or Enteric) Coating Layer

In the pharmaceutical dosage forms, the enteric coating layer is applied to the insulating layer and it contains anionic copolymers of methacrylic acid and ethyl acrylate (Eudragit® L30D, Eudragit® L30D-55, Eudragit® L100-55 of Rohm & Hass), or latex of cellulose acetophtalate (CAP), such as Aquateric® of FMC, pharmaceutically acceptable plasticizers, such as triethylcitrate (Citroflex®-2), tributylcitrate (Citroflex®-4), acetyltributylcitrate (Citroflex®-A4), dibutyl sebacate (DBS), diethylphtalate (DEP), acetylated monoglyceride (Myvacet® 9-40), polyethylenoglycols or 1,2-propylene glycol, and possibly a lubricant such as talc or colloidal silicon dioxide (Aerosil® 200 of Degussa) and an anti-foaming agent in the nature of silicone. The amounts of polymer and plasticizer have to be strictly selected in order to guarantee the intended gastroresistance.

The gastroresistant film coats each granule completely and makes the dosage form insoluble in acid media, but quickly disintegrable for neutral and alkaline pH values, as in the case of the fluids present in the proximal fraction of the small intestine, where the dissolution and absorption of the piroxicam will occur. The thickness of this layer should not be less than 20 μm, in order to guarantee effective protection.

The final product is sieved in rooms with controlled humidity and temperature, and placed in hard gelatine capsules.

The dosage forms of the present invention are multiunitary formulations in the form of pellets characterized by: a) a spherical inert core coated with several concentric layers which results in a product of spherical symmetry, b) a first layer of a thickness of 150–250 μm, applied to the inert cores, containing piroxicam mixed with pharmaceutically acceptable inert substances, c) a second layer (intermediate layer), of a polymeric nature, and d) a third layer (the outside layer), constituted by a gastroresistant or enteric polymer of a minimum thickness of 20 μm. Furthermore, the formulations are characterized by the complete absence of residues of organic solvents and the impurities associated to them.

The dosage forms produced by extrusion/spheronization methods are completely outside the scope of the present invention, because the pellets produced by those methods have preponderantly axial symmetry, whereas the dosage forms of the present invention have spherical symmetry, besides other differences of a structural nature (number of layers, presence of an inert core from which the growth of the pellet begins during its preparation, etc).

Below are some examples of formulations that were obtained during the optimization process, until the final formulations were produced.

EXAMPLES

HPMC dispersion prepared previously after cooling it to about 35° C. This last suspension was homogenized by shaking and applied to the inert cores (710–850 μm). After the application of the suspension, the pellets were dried so that their temperature did not exceed 50° C.

For the preparation of the insulating layer (2nd layer or intermediate layer), demineralized water was heated up to 85–90° C. After this temperature was reached, HPMC was added and homogenized by shaking, until total dispersion was achieved. The dispersion was cooled to room temperature and applied to the product already containing the piroxicam layer. This operation is extremely delicate,

TABLE I

Qualitative and quantitative composition of dosage forms containing piroxicam (90 ± 10 mg of piroxicam/g of pellets) according to the invention.

| COMPOSITION | Example 1 (g) | Example 2 (g) | Example 3 (g) | Example 4 (g) | Example 5 (g) | Example 6 (g) | Example 7 (g) | Example 8 (g) |
|---|---|---|---|---|---|---|---|---|
| Inert cores (710–850 μm) | 1000.00 | 1000.00 | 1000.00 | 1000.00 | 1000.00 | 1000.00 | 1000.00 | 1000.00 |
| Active layer | | | | | | | | |
| Piroxicam | 150.4 | 150.4 | 150.4 | 124.0 | 127.0 | 124.0 | 124.0 | 127.0 |
| Sodium dodecyl sulfate | 6.7 | 4.5 | 4.5 | 3.1 | 2.7 | 2.7 | 2.7 | 2.8 |
| Sodium starch glycolate | 18.0 | 11.9 | 13.3 | 5.0 | 4.3 | 4.3 | 19.7 | 4.3 |
| Hydroxypropyl methylcellulose | 44.9 | 29.9 | 19.9 | 56.3 | 50.2 | 49.3 | 49.3 | 56.0 |
| L-Hydroxypropyl Cellulose | — | — | — | 37.2 | — | 32.5 | 32.5 | — |
| Lactose | 228.8 | 102.0 | 11.9 | 48.6 | 10.9 | 26.9 | 11.5 | 3.0 |
| Emulsion 30% Simethicone | — | — | — | 1.0 | 0.9 | 0.9 | 0.9 | 0.9 |
| Insulating layer | | | | | | | | |
| Hydroxypropyl methylcellulose | — | — | — | — | 40.0 | 40.0 | 40.0 | 40.0 |
| Gastroresistant layer | | | | | | | | |
| Co-polymer of the methacrylic acid | — | — | — | — | 150.0 | 150.0 | 150.0 | 150.0 |
| Triethylcitrate | — | — | — | — | 15.0 | 15.0 | 15.0 | 15.0 |
| Emulsion 30% Simethicone | — | — | — | — | 1.0 | 1.0 | 1.0 | 1.0 |
| TOTAL | 1448.8 | 1298.7 | 1300.0 | 1275.2 | 1402.0 | 1446.6 | 1446.6 | 1400.0 |
| Assay mg/g (theoretical value) | 103.8* | 115.8* | 115.7* | 97.2* | 90.6 | 85.7 | 85.7 | 90.7 |

| Tests | Example 1 | Example 2 | Example 3 | Example 4 | Example 5 | Example 6 | Example 7 | Example 8 |
|---|---|---|---|---|---|---|---|---|
| Assay | | | | | | | | |
| (mg/g) | 55.0 | 83.1 | 65.9 | 84.0 | 70.8 | 77.1 | 79.9 | 89.8 |
| (%) | (53.0) | (71.8) | (57.0) | (86.4) | (78.1) | (90.0%) | (93.3) | (99.0) |
| Gastroresistance % | — | — | — | — | — | 99.7 | 98.7 | 97.5 |
| Dissolution (%) | — | — | — | — | — | 100.4 | 98.6 | 100.2 |

*Taking into account the fact that only one layer was applied.

The formulations presented in Examples 1–8 were obtained from inert cores coated successively with the three layers, each one with the composition presented in Table I.

The pharmaceutical formulations of the invention take the form of pellets with which hard gelatine capsules are filled. The preparation of the pellets is processed as follows. For the preparation of the layer containing the active ingredient (1st layer or active layer), a portion of demineralized water was heated up to 85–90° C. and then hydroxypropylmethylcellulose (HPMC) was dispersed in it. In another portion of demineralized water, sodium dodecyl sulfate, sodium starch glycolate, lactose, the simethicone emulsion and, finally, piroxicam in micronized form were dispersed. When the suspension became uniform, it was mixed with the because it must be guaranteed that the fluidization of the bed ensures the homogeneous coating of all the pellets, with a film of regular thickness. The gastroresistant or enteric coating layer (3rd layer or external layer) was prepared by mixing the demineralized water with the simethicone emulsion, followed by the addition of triethylcitrate and, finally, the copolymer of methacrylic acid. The dispersion was then homogenized for a few minutes and applied to the pellets already coated with the intermediate layer.

All the stages of the manufacture of the dosage forms took place in a fluid bed equipment with an inner partition device (wurster), under specific conditions.

As regards the final products, the amount of the active ingredient (mg of piroxicam/g of pellets), as well as the gastroresistance (%) and dissolution parameters of the formulations, were determined. The objective established for this invention was the obtention of a dosage form with the following characteristics: amount of active ingredient≧85 mg of piroxicam/g of pellets, gastroresistance≧95% and dissolution>90%, in order to establish the following specification limits (which should be maintained throughout the period of validity of the product): amount of active ingredient≧80.75 mg of piroxicam/g of pellets, gastroresistance≧85%, dissolution≧75%.

The analysis of the results obtained in the assays performed with the different pharmaceutical dosage forms in the Examples presented in Table I led to the following conclusions:

a) For the dosage form illustrated in Example 1, the yield obtained upon application of the first layer is not high enough to enable this formulation to be used for industrial purposes.

b) In the dosage form illustrated in Example 2, the amount of HPMC was reduced, as well as the amount of sodium dodecyl sulfate, sodium starch glycolate and, in particular, lactose. These changes increased the yield for application of the first layer to 71.8%, which is still not satisfactory.

c) Example 3 shows the influence of the amount of binders present in the first layer on the yield obtained for the application thereof. In this experiment, HPMC was reduced by more than 30% (in comparison with Example 2), and the yield for application of the active layer decreased significantly. In this case, spray drying had occurred.

d) Example 4 illustrates a formulation wherein the amount of HPMC was increased and a second binder, L-HPC, was added to the composition. At the same time, the amount of lactose was reduced to half. With this strategy, it was possible to significantly increase the yield for application of the active layer. This experiment showed that the amount of diluent and binders should be balanced in order to avoid spray drying.

e) Example 5 illustrates a formulation wherein the amount of lactose was drastically reduced, the L-HPC was completely removed and the HPMC was decreased slightly. In this case, the insulating layer, as well as the enteric layer, were also applied. The results obtained for the dosage suggest that some piroxicam was lost when the active layer was applied, which means that the amount of binder used is not enough to retain the amount of powders present in the dispersion.

f) Example 6 illustrates a dosage form wherein HPMC and L-HPC were used as binders, and a relatively low amount of lactose was also used. The insulating layer, as well as the enteric coating layer, were also applied. The values obtained for the gastroresistance and dissolution assays showed that the thickness of the insulating and enteric coating layers was well established, and the results obtained for the amount of piroxicam suggest that a good yield was reached in the process for the application of the active layer.

g) Examples 7 and 8 illustrate dosage forms wherein an attempt was made to improve the yield for application of the 1st layer, without affecting the dissolution of the dosage form. For this purpose, in Example 7 the association of HPMC-L-HPC as binders was used and the amount of lactose was reduced, but the amount of sodium starch glycolate was increased in order to guarantee adequate dissolution of the formulation. Example 8 requires the use of only one binder, HPMC, but the amount of lactose was reduced to almost zero.

h) The results obtained with the dosage forms illustrated in Example 8 suggest that the changes made to the composition of the 1st layer made it possible to increase to almost 100% the yield of the industrial process for the application of the first layer, without affecting the gastroresistance and dissolution parameters.

The Examples presented above show that it is possible, using only aqueous solvents, to obtain formulations containing piroxicam which obey the dissolution and gastroresistance criteria required for these types of dosage forms. Examples 1–5 describe dosage forms which contain a very small amount of piroxicam and are therefore non-executable from a technological point of view. Examples 6–8 describe dosage forms which are technologically executable and obey the other criteria required for a dosage form intended for development. Examples 6 and 7 describe dosage forms that obey the established criteria (i.e. GR≧85% and dissolution≧75%). However, economically these formulations are not very advantageous, because the yield for application of the 1st layer, the one that contains piroxicam, was lower than 95%. Example 8 constitutes an optimization step of the dosage forms for improving the yield of the industrial process, in order to make it economically more advantageous. Products manufactured according to the last Examples were submitted to long-term stability assays, whose results are presented below. With optimized dosage forms—final dosage forms—it will be shown that the products obtained, besides obeying analytic specifications when analysed immediately after manufacture, maintain their stability during a period of time appropriate for sale on the pharmaceutical market for therapeutic purposes.

The present invention also relates to the preparation of other piroxicam multi-unitary dosage forms, of greater potency (i.e. 145±15 mg of piroxicam/g of pellets), for treatment with higher dosages (i.e. 40 mg/capsule), also using hard gelatine capsules of small dimensions for increased patient comfort. In order to achieve this, inert cores of smaller dimensions are used (600–710 μm). Two Examples of these formulations are presented in Table II.

The preparation of the suspensions and dispersions for the manufacture of the product was carried out in the same manner as described previously. In the case of these higher potency piroxicam dosage forms, since the inert cores have smaller dimensions, it was necessary to adjust the amount of hydroxypropylmethylcellulose to be incorporated into the intermediate layer, in order to guarantee adequate isolation. It is also necessary to study the amount of enteric polymeric coating to include in the formulation, in order to obtain a layer with a thickness greater than 20 μm. All the formulations illustrated in the Examples contain an amount of active ingredient (mg/g of pellets) and gastroresistance and dissolution parameters compatible with the requirements.

TABLE II

Qualitative and quantitative composition of dosage forms containing piroxicam (145 ± 15 mg of piroxicam/g of pellets) according to the invention.

| COMPOSITION | Example 9 (g) | Example 10 (g) |
|---|---|---|
| Inert cores (600–710 μm) | 1000.0 | 1000.0 |
| Active layer: | | |
| Piroxicam | 254.0 | 254.0 |
| Sodium dodecyl sulfate | 6.1 | — |
| Sodium starch glycolate | 8.0 | 8.0 |
| Hydroxypropylmethylcellulose | 112.6 | 112.6 |
| Lactose | 6.0 | 6.0 |
| Emulsion 30% Simethicone | 1.8 | 1.8 |
| Glycerol polyethyleneglycol oxystearate | — | 16.3 |

TABLE II-continued

Qualitative and quantitative composition of dosage forms containing piroxicam (145 ± 15 mg of piroxicam/g of pellets) according to the invention.

| COMPOSITION | Example 9 (g) | Example 10 (g) |
|---|---|---|
| Insulating layer: | | |
| Hydroxypropylmethylcellulose | 70.0 | 70.0 |
| Gastroresistant layer: | | |
| Co-polymer of methacrylic acid | 260.0 | 260.0 |
| Triethylcitrate | 26.0 | 26.0 |
| Emulsion 30% Simethicone | 1.7 | 1.7 |
| TOTAL | 1146.2 | 1756.4 |
| Assay mg/g (theoretical value) | 145.5 | 144.6 |

The present invention can also be applied to other high potency NSAIDs of therapeutic interest.

Control Of The Finished Product

Parameters Analysed
Assay
Gastroresistance
Dissolution
Total impurities.

The above mentioned parameters were determined by HPLC (High Performance Liquid Chromatography), with an RP-18 column of 150 mm×46 mm, filled with particles of 5 µm, and spectrophotometric detection at λ=254 nm. The level of impurities was determined by TLC, in accordance with Pharm. Eur.

The gastroresistance assay was performed by submitting the dosage forms, for 2 hours, to the action of an acidic incubation medium of pH≈1.2, at 37° C.±0.5° C., with constant mixing at 100 r.p.m.±4 r.p.m., using the dissolution equipment described by USP.

The dissolution assay was performed by submitting the dosage forms, for 2 hours, to the action of an acidic incubation medium of pH≈1.2, at 37° C.±0.5° C., with constant mixing at 100 r.p.m.±4 r.p.m., followed by the addition of a dissolution incubation medium, maintaining the same conditions for 30 minutes, using the dissolution equipment described by USP.

Stability Tests

To test the stability of the pharmaceutical dosage forms, stability tests were performed on batches of capsules containing the pellets manufactured according to the present invention. The pellets were placed in hard gelatine capsules which were stored in blisters of polyamide/aluminium/PVC sealed with aluminium foil of 25 µm. These blisters were maintained at room temperature (real time), and also in an incubator at 40° C. and 75% relative humidity, and certain parameters were periodically determined, such as assay (amount of the active ingredient), gastroresistance, dissolution and level of impurities. The results obtained for one batch of piroxicam pellets are presented as follows.

TABLE III

BATCH MED28 - PIROXICAM PELLETS
Assays performed with product maintained at 40° C./75% relative humidity

| Incubation period (months) | Temperat. (° C.) | Relative Humidity (%) | Colour | Assay (mg/g) (%) | Gastro-resistance (%) | Dissolution (%) | Impurities (%) |
|---|---|---|---|---|---|---|---|
| 0 | 40 | 75 | A | 89.8 (100.0) | 97.5 | 100.0 | <0.2 |
| 1 | 40 | 75 | A | 89.5 (99.7) | 97.7 | 98.8 | <0.2 |
| 3 | 40 | 75 | A | 87.2 (97.1) | 94.7 | 97.3 | <0.2 |
| 4 | 40 | 75 | A | 89.8 (100.0) | 100.0 | 100.0 | <0.2 |
| 6 | 40 | 75 | A | 87.6 (97.6) | 101.4 | 102.1 | <0.2 |
| 9 | 40 | 75 | A | 89.3 (99.4) | 103.9 | 96.9 | <0.2 |
| 10 | 40 | 75 | A | 88.0 (98.0) | 94.0 | 99.4 | <0.2 |

A-Yellow
*The World Health Organisation considers that accelerated stability studies using incubation conditions of a temperature of 40° C. and 75% relative humidity for 3 months in temperate and subtropical climates and 6 months in hot climates for products that are intended for the global market are a good indicator of the stability of a pharmaceutical dosage form. (WHO/PHARM/94.565).

TABLE IV

BATCH MED28 - PIROXICAM PELLETS
Assays performed with product maintained at room temperature (real time)

| Incubation period (months) | Temperat. (° C.) | Relative Humidity (%) | Colour | Assay (mg/g) (%) | Gastro-resistance (%) | Dissolution (%) | Impurities (%) |
|---|---|---|---|---|---|---|---|
| 0 | 25 | 60 | A | 89.8 (100.0) | 97.5 | 100.0 | <0.2 |
| 6 | 25 | 60 | A | 89.6 (99.8) | 94.0 | 104.5 | <0.2 |

TABLE IV-continued

BATCH MED28 - PIROXICAM PELLETS
Assays performed with product maintained at room temperature (real time)

| Incubation period (months) | Temperat. (° C.) | Relative Humidity (%) | Colour | Assay (mg/g) | Gastro-resistance (%) | Dissolution (%) | Impurities (%) |
|---|---|---|---|---|---|---|---|
| 12 | 25 | 60 | A | 88.5 (98.6) | 97.5 | 95.7 | <0.2 |
| 18 | 25 | 60 | A | 89.8 (100.0) | 98.5 | 95.5 | <0.2 |

A-Yellow.

Discussion

The Examples presented above show that the dosage form of the present invention presents good stability during a prolonged period of storage (i.e. at least 3 years) and gastroresistance parameters adapted to the length of time that the product stays in the stomach, being quickly dissolved as soon as it reaches the proximal portion of the small intestine. For these reasons, the formulations should present the following characteristics:

1) An inert core of spherical symmetry, containing pharmaceutically acceptable inert excipients, which acts as the support on which the remaining elements of the formulation are deposited.

2) A layer containing piroxicam in micronized form mixed in an appropriate proportion with pharmaceutically acceptable inert excipients, whose properties guarantee the disaggregation of the formulation and the dissolution of the active ingredient in the chosen site.

3) A water-soluble insulating layer of a polymeric nature, which separates the active layer from the gastroresistant or enteric coating layer and prevents any interaction between them.

4) An enteric coating layer, generally constituted by an acrylic polymer, of a minimum thickness of 20 µm, possibly in the presence of a plasticizer and/or an anti-foaming agent, insoluble at the gastric pH and easily disaggregable at the pH of the proximal part of the small intestine.

5) Total absence of residues of organic solvents or the impurities associated to them, since the formulation is produced exclusively using demineralized water.

The results obtained show that the dosage forms of the present invention are stable in terms of dosage, as well as in terms of the other parameters tested (i.e. gastroresistance, dissolution and level of impurities). The process used to manufacture the products is economically advantageous and it also has novelty as regards its application. The technological process used is extremely safe, since it does not require the use of organic solvents, with a toxicity risk to operators or an explosion risk. Moreover, the pharmaceutical dosage form itself is safe, since there are no residues of organic solvents or the impurities inherent to them in the finished product, which is an advantage of this product in terms of public health.

In addition, the whole manufacturing process takes places in the same equipment, a fluid bed equipment with an inner partition device (wurster), which produces pellets with high sphericity and a flat surface, constituted by layers of uniform thickness, contrary to what happens with the pellets produced by extrusion/spheronization, by rotogranulation or in conventional coating pans.

The pharmacist can always make variations to the pellet formulations of the present invention, for example the use of other aqueous polymers to check gastroresistance, such as aqueous dispersions of cellulose acetophtalate (CAP), of other plasticizers, such as tributylcitrate (Citroflex®-4), acetyltributylcitrate (Citroflex®-A4), dibutyl sebacate (DBS), diethylphtalate (DEP), monoglyceride acetylated (Myvacet® 9-40), of other aggregants, such as methylcellulose, ethylcellulose, hydroxyethylcellulose, hydroxypropylcellulose, polyethylenoglycol, polyvinylpyrrolidone, etc., of other disaggregants, such as pregelatinized starch, microcrystalline cellulose, calcic or sodic carboxymethylcellulose or sodium alginate, or other surfactant agents, such as sodium trilaurylsulfate, sodium tridecylethoxylate, sodium myristylsulfate or sorbitane esters, without going beyond the spirit and scope of the present invention. The invention can also be applied to other NSAIDs or their pharmaceutically acceptable salts, if this can be justified in therapeutic terms.

Finally, it should be pointed out that the present invention does not cover the formulations obtained using the classic extrusion/spheronization techniques already known from the state of the art, which give rise to products that are different from those that are intended to be protected by the present invention, in terms of qualitative and quantitative composition and also in structural terms.

What is claimed is:

1. Stable pellet pharmaceutical preparations containing piroxicam characterized in that they contain an amount of active ingredient of between 5 and 50 mg, an inert core with spherical symmetry and a diameter of 600–850 µm, constituted by starch and sucrose, coated with an active layer containing piroxicam in micronized form and pharmaceutically acceptable inert excipients, mixed in appropriate proportions in order to allow the adequate disaggregation of the formulations and dissolution of the active ingredient, coated in turn with a polymeric insulating layer and soluble in water, said polymeric insulating layer being coated finally with a gastroresistant or enteric layer of a minimum thickness of 20 µm.

2. Pharmaceutical preparations according to claim 1, characterized in that the layer which contains the active ingredient contains less than 3% by weight of disaggregants, selected from the group consisting of sodium starch glycolate, pregelatinized starch, microcrystalline cellulose, sodic or calcic carboxymethylcellulose, sodium alginate, and mixtures thereof.

3. Pharmaceutical preparations according to claim 1, characterized in that the active layer containing the active ingredient contains less than 5% by weight of surfactants, selected from the group consisting of sodium dodecylsulfate, sodium trilaurylsulfate, sodium tridecylethoxylate, sodium myristylsulfate, glycerol polyethyleneglycol oxystearate, and mixtures thereof.

4. Pharmaceutical preparations according to claim 1, characterized in that the insulating layer is soluble and/or easily disaggregable in water, containing polymeric binding agent(s) present in a percentage of 2–8% by weight based upon the final weight of the product, and selected from the group consisting of methylcellulose, ethylcellulose, hydroxymethylcellulose, hydroxypropylcellulose, hydroxypropylmethylcellulose, polyvinylpyrrolidone and polyethylene glycols.

5. Pharmaceutical preparations according to claim 1, characterized in that the gastroresistant or enteric layer only contains aqueous polymers, selected from the group consisting of anionic copolymers of methacrylic acid and ethyl acrylate, and cellulose acetophthalate, present in a percentage of 8–16% by weight based on the final weight of the product, mixed with one or more pharmaceutically acceptable plasticizers, selected from the group consisting of triethylcitrate, tributylcitrate, acetyltributylcitrate, dibutylsebacate, diethylphthalate, monoglyceride acetylated and polyethylenoglycols, which are present in a percentage of between 1.0% and 2.0%, mixed with an anti-foaming agent in the nature of silicone, which is present in a percentage of less than 0.5%, and optionally a lubricant in the nature of talc or colloidal silicon dioxide.

6. Pharmaceutical preparations according to any one of claims 1–5, characterized in that they are free from organic solvents or inherent residues to them and contain an amount of water lower than 1.5% by weight.

7. Pharmaceutical preparations according to claim 6 designed in such a way that the final products display and maintain the characteristics relating to the amount of active ingredient, gastroresistance, dissolution and total impurities adequate for a period of validity of 3 years.

8. Process for the preparation of the pharmaceutical dosage forms according to claim 7, in which all the stages of their manufacture take place in a fluid bed equipment with an inner partition device (wurster), without using organic solvents in any of the phases of the technological process.

9. A method for treatment of a patient suffering from an inflammatory condition which consists of the oral administration of enteric-coated piroxicam dosage forms to a patient in need of such treatment, in a therapeutically effective quantity.

* * * * *

UNITED STATES PATENT AND TRADEMARK OFFICE
CERTIFICATE OF CORRECTION

PATENT NO. : 6,391,341 B1
DATED : May 21, 2002
INVENTOR(S) : Carla Patricia Mendes and Maria Julia de Oliveira It is certified that error appears in the above-identified patent and that said Letters Patent is hereby corrected as shown below:

<u>Title page,</u>
Item [73], please indicate the Assignee as follows:

-- [73] Assignee: Laboratorio Medinfar - Produtos Farmaceuticos, S.A., Amadora, Portugal --.

Signed and Sealed this

Thirteenth Day of April, 2004

JON W. DUDAS
*Acting Director of the United States Patent and Trademark Office*